US000002029H

(19) United States

(12) Statutory Invention Registration (10) Reg. No.: US H2029 H

Comey, III et al. (43) Published: Jun. 4, 2002

(54) ENVIRONMENTAL SAFETY APPARATUS FOR AIRBORNE HYDROGEN FLUORIDE RECOVERY AND METHOD

(75) Inventors: Kenneth Roy Comey, III, Beaumont; Gerald Verdell Nelson; Lee Kessie Gilmer, both of Nederland, all of TX (US)

(73) Assignee: Texaco Inc., White Plains, NY (US)

(21) Appl. No.: 08/143,598

(22) Filed: Nov. 1, 1993

(51) Int. Cl.[7] ..... B01J 19/00; G05D 9/00; C07C 2/58

(52) U.S. Cl. ..... 422/241; 422/228; 422/107; 585/723

(58) Field of Search ..... 422/240, 241, 422/255, 256, 228, 105, 107; 585/723, 724, 725

(56) References Cited

U.S. PATENT DOCUMENTS

| | | | | | |
|---|---|---|---|---|---|
| 2,391,148 | A | * | 12/1945 | Frey | 585/725 |
| 3,649,202 | A | * | 3/1972 | Bajek et al. | 422/62 |
| 3,751,229 | A | * | 8/1973 | Bajek et al. | 422/109 |
| 4,218,574 | A | * | 8/1980 | Anderson | 585/723 |
| 4,220,806 | A | * | 9/1980 | Mikulicz et al. | 585/723 |
| 4,243,830 | A | * | 1/1981 | Carson | 585/723 |
| 4,467,131 | A | * | 8/1984 | Washer et al. | 585/723 |
| 4,555,325 | A | * | 11/1985 | Wolowski et al. | 422/241 |
| 4,677,244 | A | * | 6/1987 | Hachmuth et al. | 422/109 |
| 4,855,112 | A | * | 8/1989 | Adcock | 422/189 |
| 4,891,466 | A | * | 1/1990 | Kocal | 585/725 |
| 4,938,935 | A | * | 7/1990 | Ander et al. | 585/725 |
| 4,938,936 | A | * | 7/1990 | Yan | 585/725 |
| 5,073,674 | A | * | 12/1991 | Olah | 585/725 |
| 5,277,881 | A | * | 1/1994 | Partridge, Jr. et al. | 422/241 |
| 5,286,456 | A | * | 2/1994 | Schatz | 422/117 |

OTHER PUBLICATIONS

Aerosol Reduction from Episodic Releases of Anhydrous HF acid by Modifying the Acid Catalyst with liquid onium, Comey et al, Presentation to Arche 1993, Summer National Meeting, Aug. 16, 1993, pp. 1–17.*

* cited by examiner

*Primary Examiner*—Michael J. Carone
*Assistant Examiner*—Aileen J. Baker
(74) *Attorney, Agent, or Firm*—Arnold White & Durkee

(57) ABSTRACT

A safety apparatus has been found for recovering an airborne hydrogen fluoride release in a hydrocarbon alkylation process. The safety apparatus comprising containment baffles and hydrogen fluoride detectors. Hydrogen fluoride detectors activate water flood means which discharge into the containment baffles. The water flood containing essentially all of the hydrogen fluoride release is recovered for disposal. Recoveries of 90 wt % have been demonstrated.

8 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

ENVIRONMENTAL SAFETY APPARATUS FOR AIRBORNE HYDROGEN FLUORIDE RECOVERY AND METHOD

CROSS-REFERENCE TO RELATED APPLICATION

This application is related to Ser. No. 07/944,619 filed Sep. 14, 1992, for Hydrogen Fluoride Alkylation Apparatus and Vapor Recovery Method to G. P. Partridge, Jr.; K. R. Comey, III; J. Mudra IV and L. K. Gilmer now U.S. Pat. No. 5,277,881.

BACKGROUND OF THE INVENTION

1. Field of the Invention

This invention is an environmental safety apparatus in combination with means for using hydrogen fluoride. The invention is also a safety method of collecting an airborne release of hydrogen fluoride.

2. Description of the Related Art

The catalytic alkylation of an isoparaffin with an olefin to produce a branched paraffin is a commercially important process for producing high octane gasoline. In general, the process comprises the reaction of an isoparaffin such as isobutane with an olefin such as propylene, 1-butene, 2-butene or mixtures thereof in the presence of a liquid acid alkylation catalyst in a reaction zone. Reaction is followed by separation of the product and unreacted hydrocarbons from the liquid alkylation catalyst in a settling zone and purification of the alkylate product. If the isoparaffin is isobutane and the olefin is a butene, the alkylate product is isooctane. Alkylate product is used to enhance the octane number of automotive gasoline and aviation gasoline.

Anhydrous hydrogen fluoride is a particularly effective catalyst for the alkylation process. Though effective, the volatility and destructive effect of hydrogen fluoride on animal tissue has curtailed expanded use of this catalyst in the petroleum refining industry due to a concern over accidental releases.

There is a need in the petroleum refining industry for an apparatus and method which will contain an accidental release of hydrogen fluoride from a major process vessel.

SUMMARY OF THE INVENTION

The invention is an environmental safety apparatus for collecting an airborne release of hydrogen fluoride from a hydrogen fluoride utilizing means.

The environmental safety apparatus comprises a containment baffle defining a volume sufficient to substantially enclose the utilizing means. At least one hydrogen fluoride detecting means is mounted within the containment baffle. Flood means has a capacity to substantially flood the containment vessel with an aqueous liquid. Means is provided responsive to detecting means to activate the flood means. Means is provided to receive the aqueous liquid from the containment baffle.

The invention is used in combination with hydrogen fluoride utilizing means such as an alkylation process vessel, containment vessel or transportation vessel to capture an accidental airborne release of hydrogen fluoride. As a result, escape of the release is prevented and damage to the environment is prevented.

BRIEF DESCRIPTION OF THE DRAWING

The Drawing is a schematic flow diagram illustrating a preferred embodiment of the invention.

DETAILED DESCRIPTION OF THE INVENTION

Figure 1:
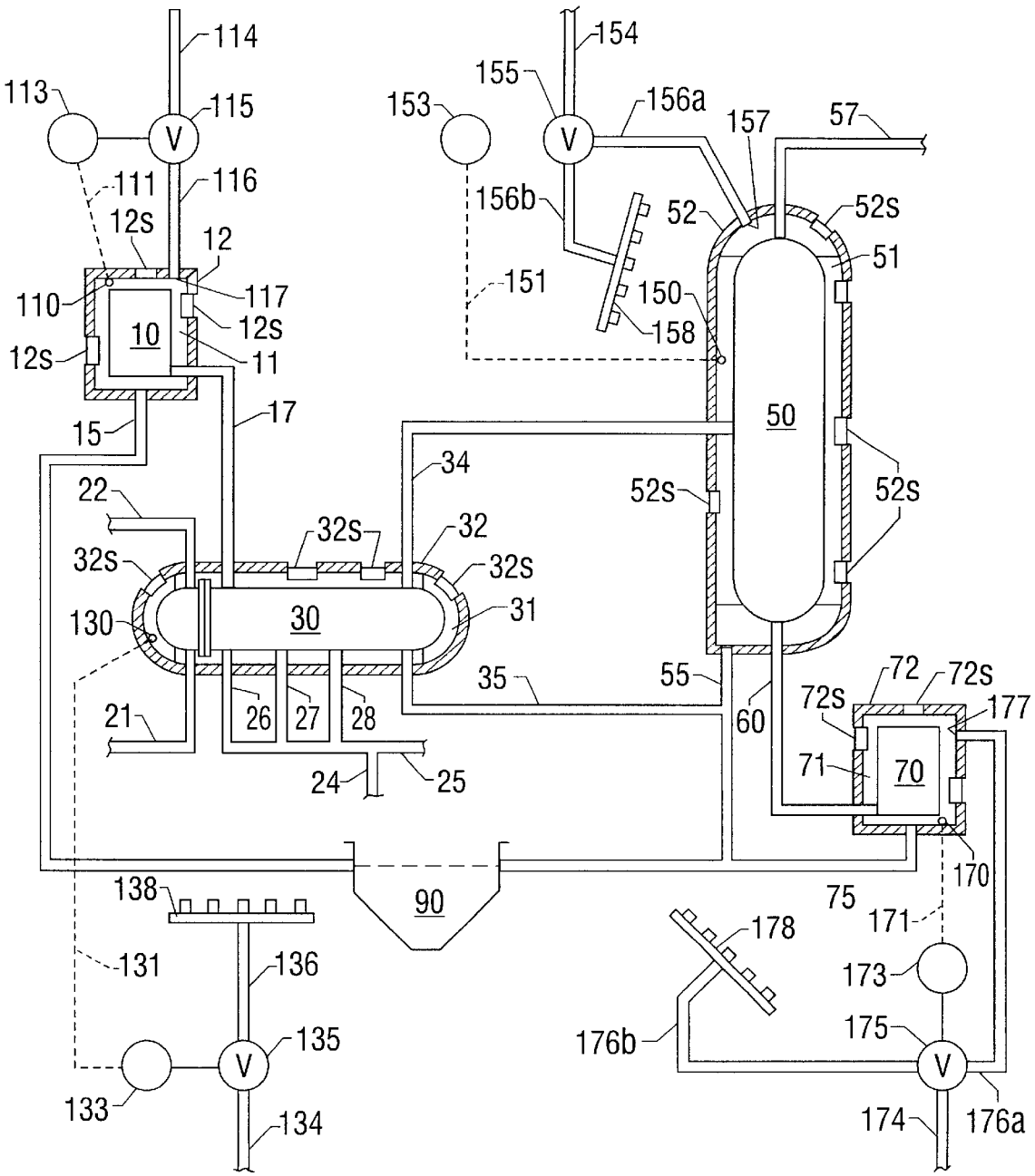

The alkylation reaction is carried out between an isoparaffin and a monoolefin in the presence of alkylation catalyst. The preferred isoparaffin is isobutane. Isopentane is also used. Common monoolefins include propylene, isobutylene, 1-butene, 2-butene, pentylenes and mixtures thereof. The preferred monoolefin is a $C_4$ olefin, typically a mixture of 1-butene, 2-butene and isobutene. A typical $C_4$ olefin mixture is one fraction from a fluid catalytic cracking process comprising about 25 vol % 1-butene, 45 vol % 2-butene and 30 vol % isobutylene. Diolefins or higher functionality olefins are to be avoided in the reaction. Higher functionality olefins alkylate at each double bond, forming polymers which are not useful for gasoline blending.

The alkylation catalyst is hydrogen fluoride, referred to in the art as hydrofluoric acid or simply by its molecular symbol HF. Generally, anhydrous hydrogen fluoride is supplied to the process. In use, a typical analysis shows 1 wt % to 2 wt % water and 5 wt % to 15 wt % acid soluble oil.

The reaction may be carried out at pressures varying from atmospheric to as high as 1000 psia (68 atm) or higher, preferably about 125 to 220 psia (8.5 to 15 atm) and at residence times of 20 seconds to 5 minutes. The pressure is selected in cooperation with the temperature to maintain the hydrocarbon reactants in liquid phase and generally ranges from −40° F. (−40° C.) to about 150° F. (66° C.). In the preferred reaction of isobutane with a $C_4$ monoolefin the reaction temperature is between about 60° F. (15° C.) and about 100° F. (38° C.) and most preferably about 90° F. (32° C.).

In the alkylation reaction a substantial molar excess of isoparaffin to olefin is employed to provide an isoparaffin/olefin feed ratio in excess of about 1/1, generally 4/1 to 70/1 and preferably 5/1 to about 20/1.

Reference is made to the Drawing. The isoparaffin feed in line 24 and the olefin feed in line 25 are combined and introduced into reactor vessel 30 via lines 26, 27 and 28. Fresh, anhydrous hydrogen fluoride in tank 10 is passed via line 17 into reactor vessel 30 which is either horizontally or vertically elongated and cylindrical in shape. The volume of anhydrous, liquid hydrogen fluoride exceeds the volume of the isoparaffin and monoolefin mixture. The liquid hydrogen fluoride constitutes a continuous phase in reactor vessel 30 and the hydrocarbon feedstocks constitute a discontinuous phase. Coolant, such as cooling water is passed via line 21 through heat exchanger tubes (not shown) exposed to the reaction mixture in reactor vessel 30, thereby moderating reaction temperature to the selected range. Coolant is discharged via line 22.

Reaction effluent, comprising alkylate product, unreacted isoparaffin and liquid catalyst are withdrawn from reactor vessel 30 via line 34 and discharged into catalyst settler vessel 50 which is vertically elongated and cylindrical in shape. The catalyst settler vessel 50 allows for separation of the reaction effluent from the alkylation reactor into an upper liquid hydrocarbon phase and a lower liquid catalyst phase containing hydrogen fluoride catalyst, acid soluble oil, and water. The catalyst settler vessel 50 may contain separation trays and vertical downcomers (not shown) positioned within the vessel to enhance separation.

The alkylate product phase is withdrawn via line 57 and processed by fractional distillation (not shown) to recover unreacted isoparaffin and alkylate product.

The liquid catalyst phase is withdrawn via line 60 and passed to spent acid tank 70. A portion of this acid may be recycled (not shown) from spent acid tank 70 to reactor vessel 30.

Surrounding and enclosing each of the major process vessels is a containment baffle. The containment baffle allows for a vapor space between the vessel and the baffle. Fresh acid tank 10 is enclosed by containment baffle 12, providing vapor space 11 and fluid communication with the air via slots 12s. Reactor vessel 30 is enclosed by containment baffle 32, providing vapor space 31 and fluid communication with the air via slots 32*s*. Acid catalyst settler 50 is enclosed by containment baffle 52, providing vapor space 51 and fluid communication with the air via slots 52*s*. Spent acid tank 70 is enclosed by containment baffle 72, providing vapor space 71 and fluid communication with the air via slots 72*s*.

Each of the vessels is cylindrical in shape as is each containment baffle. Preferably each containment baffle has a cylindrical radius 0.25 inches (0.635 cm) to 36 inches (91.44 cm) greater than the cylindrical radius of the vessel. Should a major process vessel leak, the vapor space provides volume for hydrogen fluoride to collect while limiting escape to the atmosphere via the slots. Hydrogen fluoride vapor at an initial escape velocity of 50 ft./sec. to 1500 ft./sec. has been found to condense on the baffle at atmospheric temperature and pressure, forming a vapor-condensate mixture.

The containment baffles dissipate the momentum of the escaping hydrogen fluoride vapor and reduce the velocity of the vapor-condensate mixture to that of the ambient air or less, generally 0 to 15 miles/hr. (22 ft./sec.), typically 0 miles/hr (0 ft./sec.) to 5 miles/hr. (7.3 ft./sec.).

This slow moving mixture under the containment baffle is sufficiently concentrated that it is detectable by detecting means. Commercially available hydrogen fluoride composition detectors are sufficiently sensitive to react to concentrations of 1 part per billion parts by weight to 1 part per million by weight in 15 seconds to 1 minute. This threshold is below the concentration of 20 parts per million by weight considered an immediate danger to life and health by the National Institute of Occupational Safety and Health. As little as 50 parts per million parts by weight is considered lethal. Secondary hydrogen fluoride detecting means includes hydrocarbon detectors and temperature and pressure sensors. A massive release would be indicated by the presence of hydrocarbon or a sudden or large temperature or pressure change under an impingement baffle. For example, a temperature change of 10° F. (5.5° C.) or more or a pressure change of 1 psi or more would indicate a vapor release.

Primary, composition detectors and secondary detectors are shown as detector 110 associated with tank 10, detector 130 associated with reactor vessel 30, detector 150 associated with catalyst settler vessel 50 and detector 170 associated with spent acid tank 70. It is understood that the drawing is schematic and an array of detectors may be distributed within each containment baffle. Such an array would incorporate both primary, composition detectors and secondary detectors including hydrocarbon detectors, thermocouples and pressure sensors.

Each detector produces a signal when activated by the presence of hydrogen fluoride. Detector 110 produces signal 111 which is transmitted to valve actuator 113. Valve actuator 113 actuates quick open valve 115 providing a flood of aqueous liquid from water supply 114 into containment baffle 12 via flood line 116. The aqueous liquid is water. Incorporated in the liquid water may be alkali agents, buffers and surfactants to improve effectiveness in dissolving and neutralizing hydrogen fluoride. The water is passed via fog nozzle 117 which is representative of a plurality of fog nozzles positioned around containment baffle 12. Fog nozzles are available which produce water mists having an average droplet size of 300 micron to 2000 micron and greater. This droplet size provides a large amount of surface area for the capture of hydrogen fluoride vapor.

The hydrogen fluoride dilute aqueous liquid is passed via drain line 15 to vented sump 90 where it is collected. Vapor recoveries up to 90% have been demonstrated experimentally with water/hydrogen fluoride vapor ratios of 6/1 to 40/1 by weight.

Likewise detector 130, signal 131, actuator 133, water supply 134, quick open valve 135, flood line 136 and external spray head 138 are shown. Likewise detector 150, signal 151, actuator 153, water supply 154, quick open valve 155, flood line 156*a*, flood line 156*b*, fog nozzle 157 and external spray head 158 are shown. Likewise detector 170, signal 171, actuator 173, water supply 174, quick open valve 175, flood line 176*a*, a flood line 176*b*, fog nozzle 177 and external spray head 178 are shown. The drawing is schematic and each vessel may contain a plurality of fog nozzles and external spray heads.

Hydrogen fluoride dilute aqueous liquid is passed via drain lines 35, 55 and 75 to vented sump 90 where it is collected. Sump 90 may be used in combination with ground containment means such as earthen, concrete and asphaltic dikes.

U.S. Pat. No. 5,073,674 to Olah incorporated herein by reference discloses catalytic alkylation using liquid onium polyhydrogen fluoride complexes. These compositions show less volatility at alkylation conditions than anhydrous hydrogen fluoride. These complexes in combination are therefore more susceptible to recovery by water flood and are the Best Mode for carrying out the invention contemplated by inventors.

While particular embodiments of the invention have been described, it will be understood, of course, that the invention is not limited thereto since many modifications may be made, and it is, therefore, contemplated to cover by the appended claims any such modification as fall within the true spirit and scope of the invention. For example, hydrogen fluoride utilizing means is understood to include vessels for carrying out hydrogen fluoride manufacture, fluorocarbon manufacture, fluorination, and the aromatic alkylation process.

What is claimed is:

1. Environmental safety apparatus for collecting an airborne release of hydrogen fluoride from hydrogen fluoride utilizing means comprising:

a containment baffle defining a volume sufficient to substantially enclose said hydrogen fluoride utilizing means;

at least one hydrogen fluoride detecting means mounted within said containment baffle;

flood means to substantially flood said containment baffle with an aqueous liquid;

means responsive to said detecting means to activate said flood means; and means to receive said aqueous liquid from said containment baffle.

2. The safety apparatus of claim 1 comprising an array of detecting means distributed within said containment baffle.

3. The safety apparatus of claim 1 wherein said flood means comprises a plurality of fog producing nozzles sufficient in number to substantially immediately fog the entire volume of said containment baffle.

4. The safety apparatus of claim 1 wherein said hydrogen fluoride detecting means comprises a composition analyzer.

5. The safety apparatus of claim 1 wherein said hydrogen fluoride detecting means comprises a thermocouple.

6. The safety apparatus of claim 1 wherein hydrogen fluoride utilizing means comprises an alkylation apparatus.

7. The safety apparatus of claim 1 wherein hydrogen fluoride utilizing means comprises a containment vessel.

8. The safety apparatus of claim 1 wherein hydrogen fluoride utilization means is a transportation vessel.

* * * * *